(12) United States Patent
Wilson et al.

(10) Patent No.: US 9,283,104 B1
(45) Date of Patent: Mar. 15, 2016

(54) FOOT BRACE AND METHOD OF MAKING THE SAME

(71) Applicants: Jason Burke Wilson, Cedar Creek, TX (US); Jeremy J. Janisse, West Bend, WI (US); Sean Eric Wilson, Franklin, WI (US); Dennis Jay Janisse, West Bend, WI (US); Erick Joseph Janisse, Fenton, MO (US)

(72) Inventors: Jason Burke Wilson, Cedar Creek, TX (US); Jeremy J. Janisse, West Bend, WI (US); Sean Eric Wilson, Franklin, WI (US); Dennis Jay Janisse, West Bend, WI (US); Erick Joseph Janisse, Fenton, MO (US)

( * ) Notice: Subject to any disclaimer, the term of this patent is extended or adjusted under 35 U.S.C. 154(b) by 137 days.

(21) Appl. No.: 13/938,137

(22) Filed: Jul. 9, 2013

Related U.S. Application Data

(60) Provisional application No. 61/670,006, filed on Jul. 10, 2012.

(51) Int. Cl.
*A61F 5/00* (2006.01)
*A61F 5/01* (2006.01)

(52) U.S. Cl.
CPC .................................. *A61F 5/0127* (2013.01)

(58) Field of Classification Search
CPC . A61G 13/12; A61G 13/123; A61G 13/1235; A61G 13/1245; A61G 1/01; A61G 13/125; A61F 13/00; A61F 13/061; A61F 5/05841; A61F 5/0104; A61F 5/0118; A61F 5/50; A61F 5/3761; A61F 5/3776; A61F 7/075; A61F 7/0755; A61M 5/52
USPC ...................................................... 602/23–28
See application file for complete search history.

(56) References Cited

U.S. PATENT DOCUMENTS 7,618,387 B2 * 11/2009 Buethorn ......................... 602/23
7,691,076 B2 * 4/2010 Castro .............................. 602/23

* cited by examiner

*Primary Examiner* — Michael Brown
(74) *Attorney, Agent, or Firm* — Plager Schack LLP (57) ABSTRACT

A foot brace is configured to be worn beneath a patient's ankle while meeting therapeutic goals of the patient. The foot brace includes a supportive shell made to a model of a patient's foot and possessing a medial counter, a lateral counter and an Achilles groove, which are formed to place pressure on sides of a patient's foot to meet the therapeutic goals of the patient. The shell is attached to a lining, a portion of which is mechanically coupled to a midfoot instep closure. The midfoot instep closure can place pressure on the foot of a patient to meet the therapeutic goals of a patient. The shell is attached to a rearfoot extrinsic post. The heel post pressure on the heel of a patient to meet the therapeutic goals of a patient.

6 Claims, 6 Drawing Sheets

FOOT BRACE AND METHOD OF MAKING THE SAME

RELATED APPLICATION

This application claims priority to provisional patent application U.S. Ser. No. 61/670,006 filed on Jul. 10, 2012, the entire contents of which is herein incorporated by reference.

BACKGROUND

The embodiments herein relate generally to devices that assist a user with foot problems.

Millions of people suffer from painful foot and ankle problems such as arthritis, tendinitis, and overuse injuries. Prior to the disclosed invention, either a custom made brace or off-the-shelf brace was prescribed by physicians to help treat various types of foot and ankle conditions. Unfortunately, there is a stigma in our society attached to wearing an orthotic device since others can easily see the orthotic device. Oftentimes people are hesitant to or simply refuse to utilize traditional bracing systems, as these bracing systems are bulky, difficult to conceal with clothing and draw attention to these braces. Failure to wear these braces not only wasted time and money, but also significantly prolonged the time that patients are limited by foot and ankle pain. One obstacle exacerbating this problem has been a refusal by the insurance industry to cover treatment for orthotic devices that did not extend above a user's ankle regardless of demonstrated therapeutic effects. As a result, very limited research has been done on the orthotic devices that do not extend above a user's ankle, prior to embodiments of the disclosed invention. The prior art includes: a foot orthosis designed at University of California at Berkeley Biomechanics Laboratory commonly called the "UCBL foot brace" described in detail in Inman, Vt., *UC-BL dual axis ankle control shoe insert; biomechanical considerations* BULL. PROSTHET. RES 1969; 10(11): 130-145; and U.S. Pat. Nos. 6,155,997 and 6,443,919 issued to Castro (collectively "Castro"). Castro is commonly called the "Arizona Brace."

The UCBL foot brace is a rigid, deep, plastic heel cup that offers only a fraction of the control provided by the intimate fit and integrated lacing system of embodiments of the present invention. A common complaint from patients while using a UCBL foot brace is that it is very uncomfortable and often causes painful blisters and sores due to the rigidity and lack of flexure of the thermoplastic. Furthermore, the UCBL foot brace offers only minimal side-to-side and torsional motion control of the hindfoot. When compared to embodiments of the present invention, the UCBL foot brace is much bulkier and causes shoe-fitting issues.

Embodiments of the present invention are thinner, overall structurally stronger, and more comfortable. Embodiments of the present invention offer better and more hindfoot control in all three planes of motion than the UCBL foot brace. Embodiments of the present invention can be worn in practically any style of shoe thereby improving patient compliance and increasing rates of usage.

Castro is significantly bulkier and takes up much more room in a shoe than embodiments of the present invention. Patients using Castro are often limited in footwear selection to roomy, orthopedic shoes and are often unable to utilize commercially available, fashionable and/or lightweight shoes. The weight of Castro is approximately two to four times that of embodiments of the present invention due to inefficient material working procedures, which can be a concern for elderly patients.

Castro further severely restricts ankle dorsiflexion and plantarflexion—integral components of normal ambulation. This restriction can have a major negative impact if the user does not need this restriction or is in any way unstable or has balance/proprioception deficiencies. Embodiments of the present invention provides exceptional medial-lateral and torsional control while not inhibiting normal dorsiflexion/plantarflexion of the ankle Even when some embodiments of the present invention are constructed with supramalleolar supports to augment medial-lateral control; embodiments of the present invention still do not impact dorsiflexion or plantarflexion at the ankle Embodiments of the present invention enable a clinician to create a foot brace that can be worn discretely within a patient's shoe while obtaining therapeutic effects of over-the-ankle braces.

SUMMARY

A foot brace is configured to be worn beneath a patient's ankle while meeting therapeutic goals of the patient. The foot brace includes a shell casted to conform to a patient's foot possessing a medial counter, a lateral counter and an Achilles groove which are formed to place pressure on sides of a patient's foot to meet the therapeutic goals of the patient. The shell is attached to a liner, a portion of which is mechanically coupled to a midfoot instep closure. The midfoot instep closure can place pressure on the foot of a patient to meet the therapeutic goals of a patient. The shell is attached to a rearfoot extrinsic post. The heel post pressure on the heel of a patient to meet the therapeutic goals of a patient.

The midfoot instep closure further comprises a plurality of eyelets that can accommodate laces, which can be tightened or loosened to respectively increase or decrease pressure on the tongue which can assist the shell and the rearfoot extrinsic post in meeting the therapeutic goals of the patient. In some embodiments, the supportive material is extended on the medial and lateral sides of the shell proximate the patient to provide further control of the foot and ankle.

A method of making a foot brace enables a clinician to create the foot brace that can be worn discretely beneath a patient's shoe while obtaining therapeutic effects of over-the-ankle braces. The method can include the following steps: First, a clinician casts a negative model of a patient's foot. Next, the clinician fills the negative model with a casting material which hardens into a positive mold. After this the clinician forms a shell upon the positive mold. Then, the clinician molds a thermoplastic portion of the shell over a soft interface. Next, the clinician attaches a rearfoot extrinsic post to the shell. The clinician can then cover an interior of the shell with an interior lining. After this the clinician can cover an exterior of the shell with a lining. Then, the clinician can attach a midfoot instep closure to the interior lining.

BRIEF DESCRIPTION OF THE FIGURES

The detailed description of some embodiments of the invention will be is made below with reference to the accompanying figures, wherein like numerals represent corresponding parts of the figures.

DETAILED DESCRIPTION OF CERTAIN EMBODIMENTS

Figure 1:
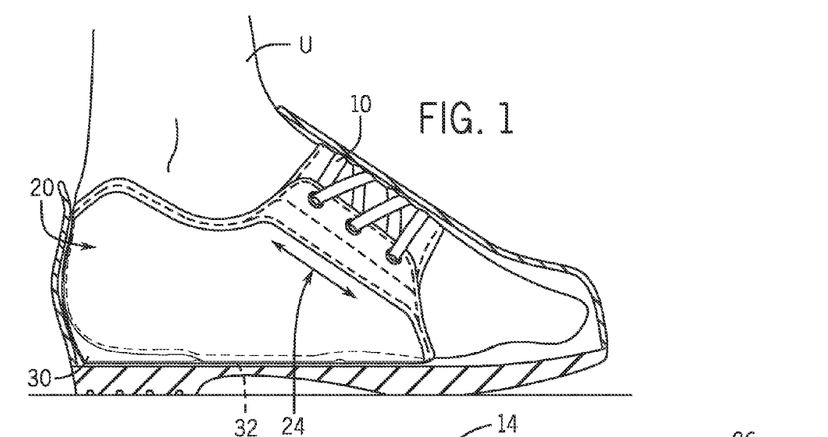
FIG. 1 shows a schematic section view of one embodiment of the present invention in use

By way of example, and referring to FIG. 1, user U, a patient desires to wear a foot brace for a therapeutic effect on the patient's foot underneath shoe S, which completely conceals the foot brace below the patient's ankle. The foot brace comprises shell 20 mechanically coupled to itself with midfoot instep closure 10. Shell 20 has an outside portion which is mechanically coupled to rearfoot extrinsic post 30 that sits proximate a rearfoot of user U and shell 20 has an inside portion which is mechanically coupled to rearfoot liner 32.

Figure 2A:
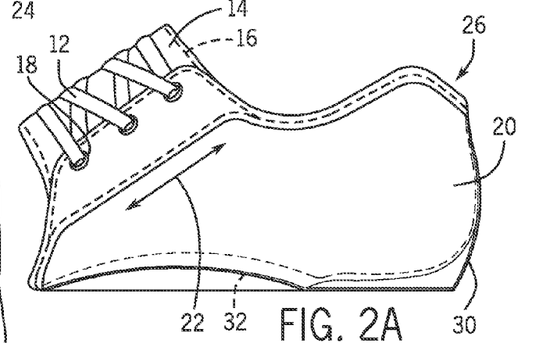
FIG. 2A is a right side plan view of an embodiment of the invention.
Figure 2B:
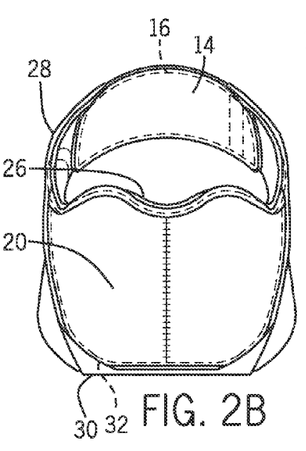
FIG. 2B is a rear plan view of an embodiment of the invention.
Figure 2C:
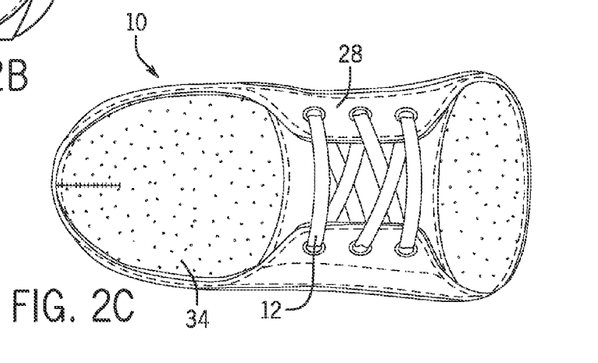
FIG. 2C is a top plan view of an embodiment of the invention.

FIG. 2A, FIG. 2B and FIG. 2C show embodiments of the foot brace in more detail. Shell 20 comprises medial counter 22, lateral counter 24 and Achilles groove 26 which are formed to meet therapeutic goals of user U. Shell 20 is mechanically coupled to lining 28, a portion of which mechanically coupled to midfoot instep closure 10. Midfoot instep closure 10 is shown here as a lacer, but any closure such as snaps, hook and loop fasteners or magnets among others can be used. In some embodiments, lining 28 can be a comfortable leather lining.

Midfoot instep closure 10 comprises tongue 14 affixed to lining 28 with stitching 16. Midfoot instep closure 10 further comprises a plurality of eyelets 18 that can accommodate laces 12 which can be tightened or loosened to respectively increase or decrease pressure on tongue 14 which can assist shell 20 and rearfoot extrinsic post 30 in creating a rearfoot extrinsic foot post pressure to obtain a therapeutic effect on user U.

In addition to the unique combination of therapeutic features beyond what was present in Castro and the UCBL foot brace, the present invention further comprises comfort features that encourage user U to wear the foot brace. For instance, the bottom of shell 20 is covered with rearfoot liner 32 and further covered with interior lining 34 to provide comfort for user U. A comfort material, such as leather on the medial and lateral sides of shell 20 proximate user U can provide further comfort for user U.

As noted above, Castro and the UCBL foot brace suffered from poor manufacturing techniques. FIG. 3A to FIG. 9B cover one theory of how to make the foot brace.

Figure 3A:
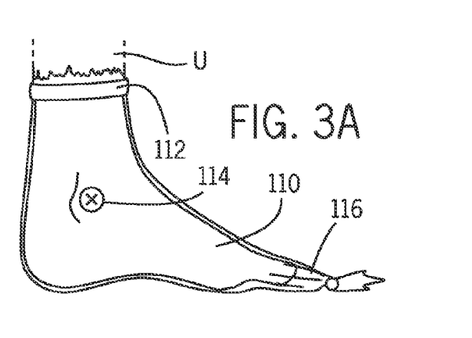
FIG. 3A shows a process step involved in producing an embodiment of the invention.

The following figures explain an exemplary method for making embodiments of the disclosed invention. FIG. 3A demonstrates marking steps. A clinician slides stockinet 110 onto the foot and/or leg of user U. The clinician then ties off distal end 116 of stockinet 110 and tapes proximal end 112 to ensure stockinet 110 does not shift during the casting process.

Figure 3B:
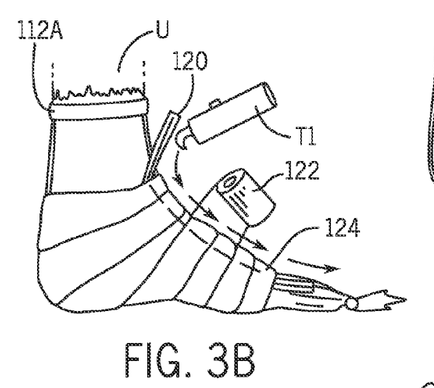
FIG. 3B shows a process step involved in producing an embodiment of the invention.

The clinician next uses an indelible pencil to mark all necessary landmarks on foot and ankle. For instance, the clinician should mark any trim line and bony landmark that the clinician perceives may be a pressure/rubbing area in the foot brace. These markings 114 should include: medial malleoli, lateral malleoli, and the watershed of the Achilles tendon, which can be used to form medial counter 22, lateral counter 24 and Achilles groove 26. FIG. 3B demonstrates the fiberglass wrap casting technique. This negative mold is then filled with plaster to create a positive model of the foot over which the brace is constructed.

Figure 4:
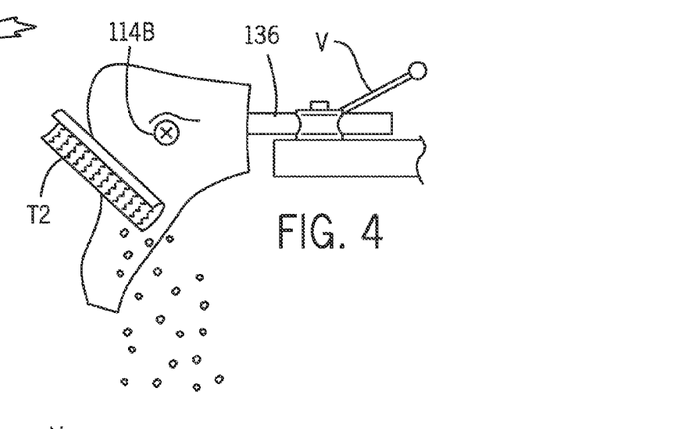
FIG. 4 shows a process step involved in producing an embodiment of the invention.

The clinician should ensure that all markings 114 were transferred from the negative cast onto the positive model. Turning to FIG. 4, the clinician can utilize hand rasp tool T2 to shape, blend, and remove plaster from the positive mold to desired needs and fit of patient.

Figure 5A:
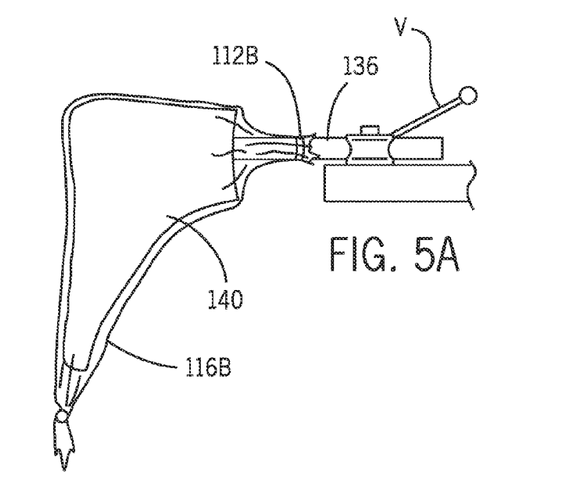
FIG. 5A shows a process step involved in producing an embodiment of the invention.
Figure 5B:
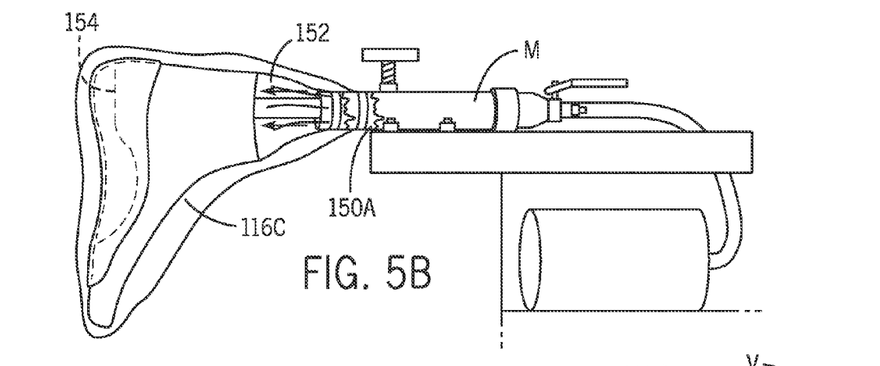
FIG. 5B shows a process step involved in producing an embodiment of the invention.
Figure 5C:
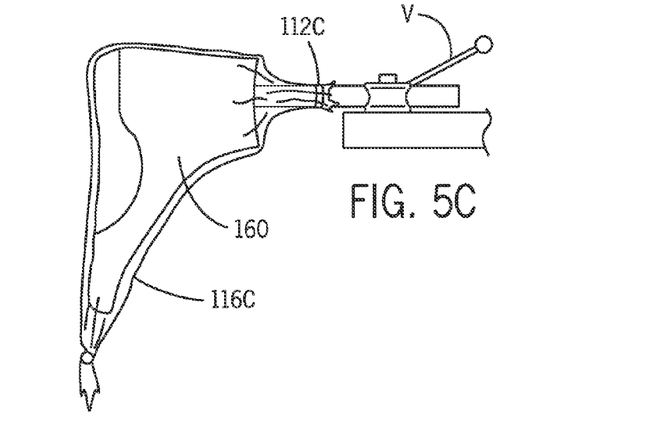
FIG. 5C shows a process step involved in producing an embodiment of the invention.

FIG. 5A, FIG. 5B and FIG. 5C provide exemplary instructions for forming a shell 20 with EVA. EVA is the copolymer of ethylene and vinyl acetate.

Turning to FIG. 5A, the EVA forming steps begin with placing pipe 136 into vise V and locking pipe 136 into place with toes facing the ground. The clinician then covesr with stockinet 116B, tying off at toes and around pipe 136.

Turning to FIG. 5B, the clinician heats EVA in oven and places EVA layer 154 onto cast 158 with another stockinet 116C over EVA layer 154. The clinician then places bag 152 over stockinet 116C.

The clinician turns on vacuum M immediately and utilizes tape 150A circumferentially around bag 152 and pipe 136, creating a vacuum seal. This causes EVA layer 154 to mold intimately to positive mold 158.

Once EVA layer 154 is cooled the clinician can release bag 152 and retrieve EVA layer 154. The clinician can now cut, trim and bevel EVA layer 154 to obtain coverage throughout the medial arch and heel cup and balance EVA layer 154. This will allow for redistribution of medial corrective forces on the foot.

Turning to FIG. 5C, the clinician can now place EVA layer 154 onto cast 158 with stockinet 116C as described above. This secures EVA layer 154 into position for next step of fabrication.

Figure 6A:
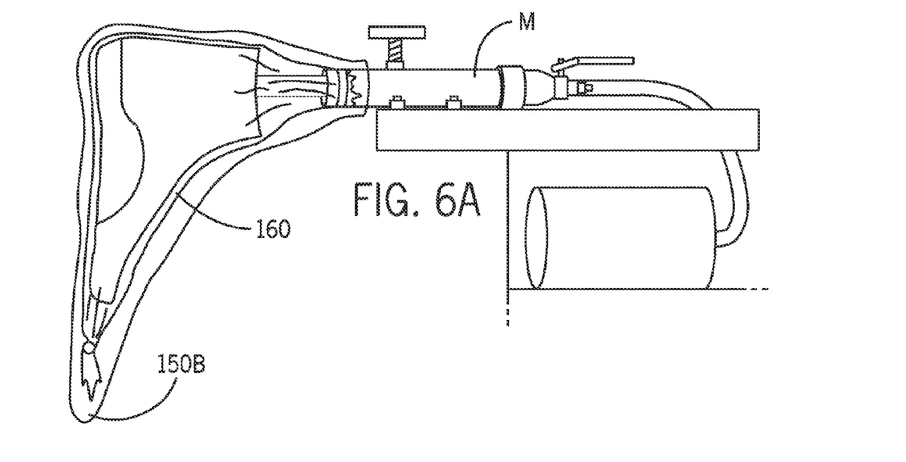
FIG. 6A shows a process step involved in producing an embodiment of the invention.
Figure 6B:
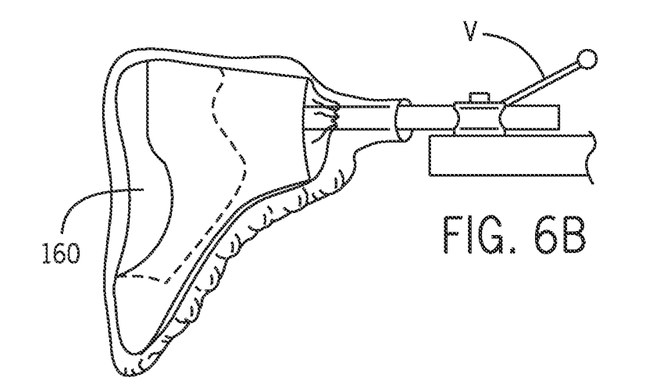
FIG. 6B shows a process step involved in producing an embodiment of the invention.
Figure 6C:
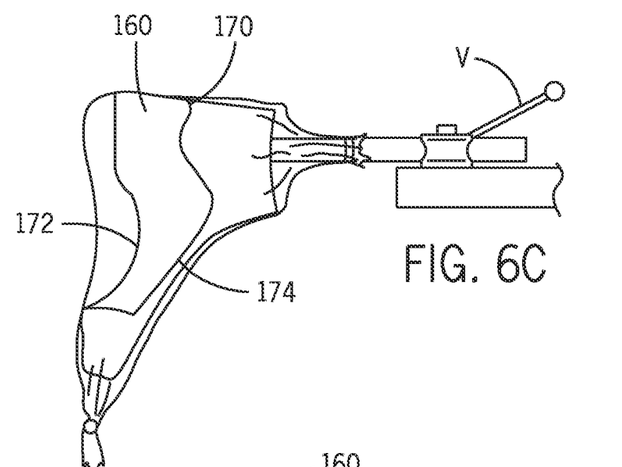
FIG. 6C shows a process step involved in producing an embodiment of the invention.

FIG. 6A, FIG. 6B and FIG. 6C show steps to make a plastic portion of the shell. Many kinds of plastic are effective including polypropylene, copolymers, and polytetrafluoroethylene which is sold under the trademark TEFLON®.

Turning to FIG. 6A, the clinician should cut to size a 3/32 inch piece of plastic allowing sufficient length to meet pipe and extend past the end of the plaster mold. The width should be based on circumferential measurement of the instep of the foot. The clinician can then place the plastic in an oven set to appropriate temperature and heat until the plastic is translucent in appearance.

At this point the clinician can turn on vacuum M and use oven gloves to remove the plastic from the oven. The clinician can drape plastic 160 around pipe 136, then, in a downward motion around positive mold 158, starting at the top and working down to toes, EVA layer 154 is not immediately covered.

Turning to FIG. 6B, the clinician should quickly make full contact seam on the dorsum of positive mold 158 to create a vacuum seal, try not to stretch or wrinkle plastic 160 during the process. After this seal plastic 160 around pipe 136 creating the final vacuum seal. This process creates a full circumferential intimate fit the positive mold and will auto fuse the EVA layer 154 into plastic 160.

Standard trim lines are as follows: Medial line 172 and lateral line 172 (not shown) are cut below the malleoli. Plastic 160 is cut with posterior line 170 below the water shed of the Achilles tendon. Medial flange line 174 and lateral flange line 174 are cut slightly wrapping towards the dorsum of the foot fully encompassing the foot and ending proximate to the metatarsal heads. Using an oscillating saw, the clinician can cut out the plastic according to the above indicated trim lines and remove excess plastic from positive mold 158.

As shown in FIG. 6C, the clinician can use a drum sander to sand rough cut edges of plastic shell 160. Using a buffing wheel, the clinician can buff and polish finished edges of plastic shell 160. The clinician then places plastic shell 160 back onto positive mold 158 and back into pipe 136 and into vice V.

Figure 7:
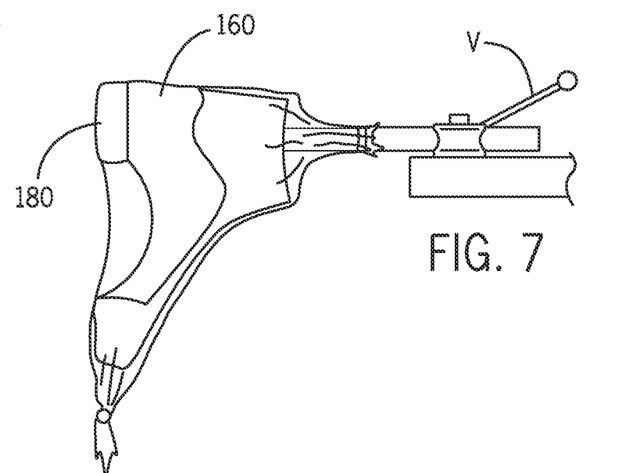
FIG. 7 shows a process step involved in producing an embodiment of the invention.

FIG. 7 shows explanatory steps to making rearfoot extrinsic post 30. To make rearfoot extrinsic post 30, a clinician cuts to size, a one half inch piece of high density EVA. EVA post 180 is sufficiently large to cover around the calcaneus stopping proximate the breast of the calcaneus.

The clinician can then lightly sand the entire heel area of plastic shell 160 to allow proper adhering of EVA post 180. The clinician can cement both plastic shell 160 and the EVA post 180 separately and let them dry. After this the clinician can place EVA post 180 into oven to manipulate moldable properties.

When pliable, the clinician can place EVA post 180 plastic shell 160 and pull nylon stockinet 116D over plastic shell 160 and positive mold 158. A clinician can turn on vacuum M immediately and then tape circumferentially around bag and pipe, creating a vacuum seal as discussed above. EVA post 180 will mold intimately to plastic shell 160. After this the clinician can release the bag and retrieve the plastic shell 160 now affixed to EVA post 180. The clinician can cut and bevel sides to blend EVA post 180 to walls of plastic shell 160 and sand/flatten the bottom of EVA post 180 to balance the heel and maximize medial/lateral control on heel strike and in stance.

Figures 8A, 8B, 8C:
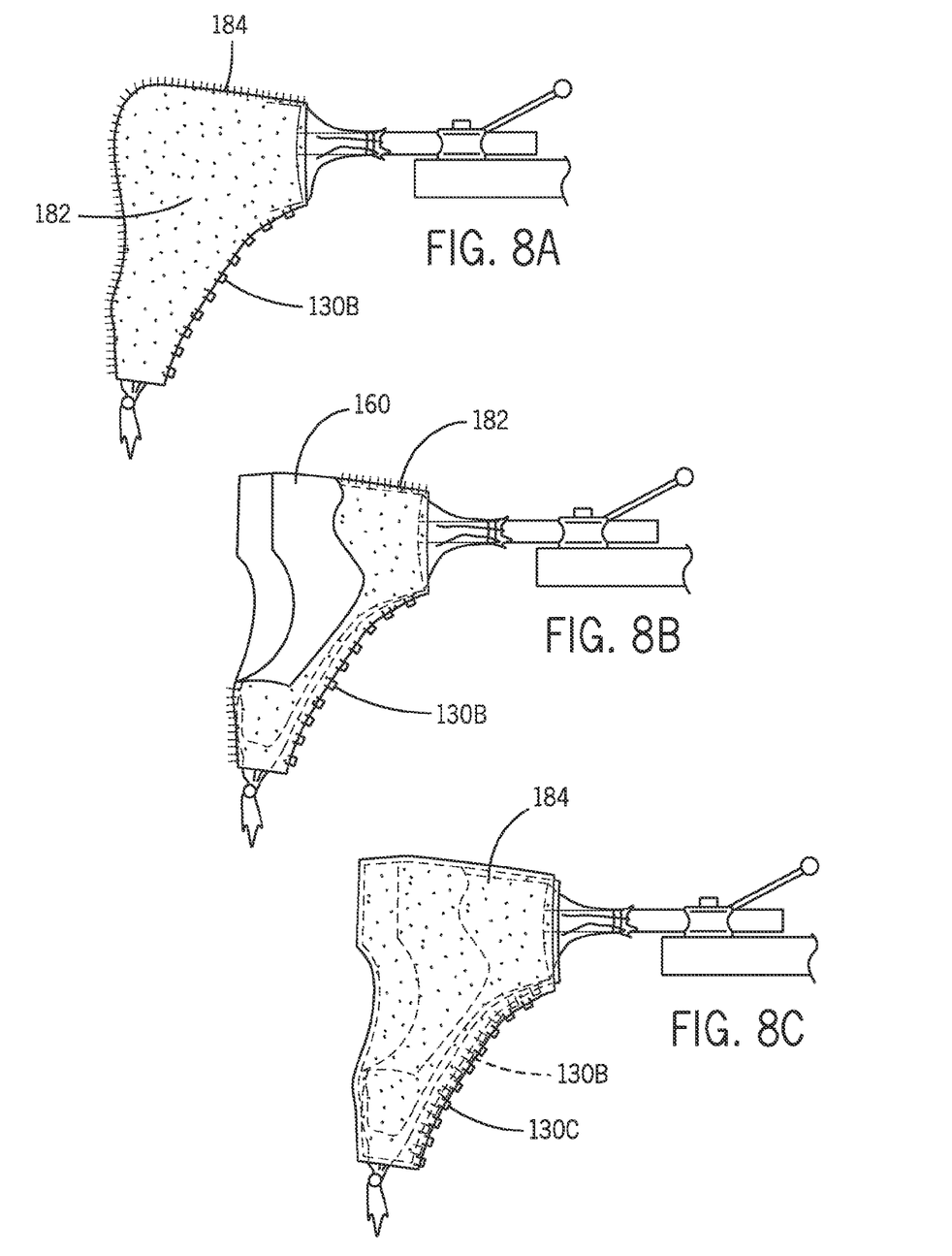
FIG. 8A shows a process step involved in producing an embodiment of the invention.
FIG. 8B shows a process step involved in producing an embodiment of the invention.
FIG. 8C shows a process step involved in producing an embodiment of the invention.

FIG. 8A and FIG. 8B show the steps to attach leather lining 182 onto the inside of plastic shell 160. The clinician cuts to size a 2.5 ounce calf skin lining leather to appropriate size for full circumferential coverage of the positive mold 158. The clinician then sews lining leather 182 so that seam 184 is posterior in position on the heel of the positive mold. Leather lining 182 has a smooth side and a coarse side as is known in the art.

Turning to FIG. 8A, the clinician then pulls leather lining 182 taught such that the smooth side is over positive mold 158 starting at the plantar side pulling to the dorsal side of positive mold 158. The clinician can then affix leather lining 182 together using staple 130B into position on the dorsal side, top to bottom, down the center of positive mold 158. This securing the position in preparation for the next step in fabrication.

Turning to FIG. 8B, the clinician can next dry fit plastic shell 160 to lining leather 182 around positive mold 158. After finding a desired finished position on positive mold 158, the clinician can make device alignment lines crossing plastic shell 160 onto lining leather 182.

After this the clinician can apply cement separately to both plastic shell 160 and leather lining 182. While the cement is damp, the clinician can slide plastic shell 160 onto leather liner 182. A final position of leather liner 182 should be consistent with the device alignment lines.

Turning to FIG. 8C, after leather liner 182 is complete leather 184 can be placed on the outside of plastic shell 160 The clinician can sew leather 184 so that the seam is posterior in position on the heel. The clinician can then apply cement to both the leather 184 and plastic shell 160 separately.

The clinician can pull leather 184 taught with the smooth side to the outside over plastic shell 160 starting at the plantar side pulling to the dorsal side of plastic shell 160. The clinician can then affix leather 184 together using staple 130C into position on the dorsal side, top to bottom, down the center of plastic shell 160. This secures leather 184 in position in preparation for the next step in fabrication.

Figure 9A:
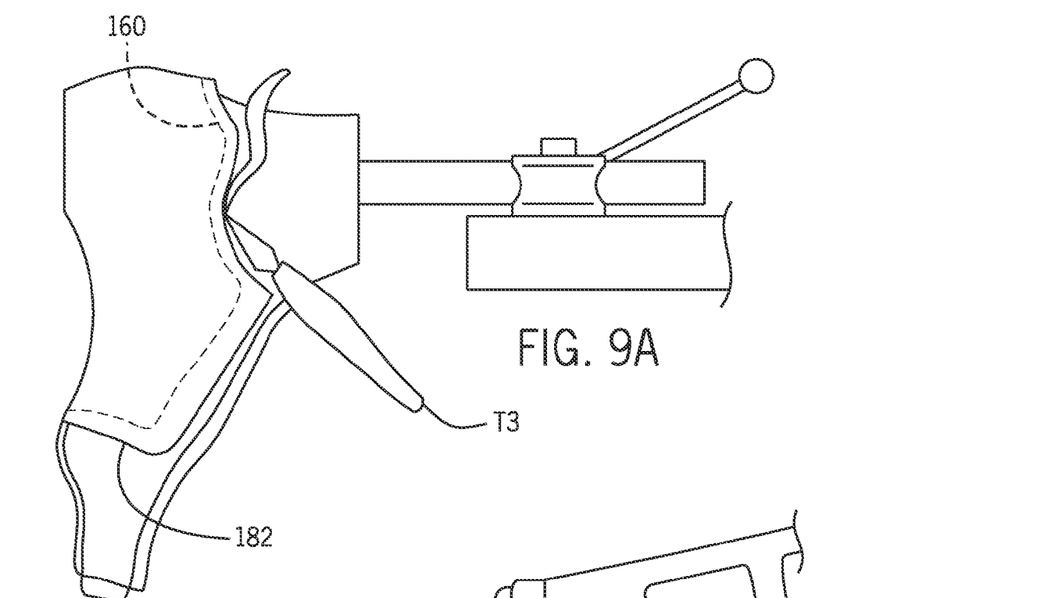
FIG. 9A shows a process step involved in producing an embodiment of the invention.

Turning to FIG. 9A, the clinician can follow the top trim lines indicated by plastic shell 160 allowing leather liner 182 and leather liner 184 to overlap by ⅜ inch. The clinician can cut along this trim line with utility knife T3, extending dorsally over the medial counter 22, lateral counter 24 and Achilles groove 26 to allow for lace stays. The clinician can remove shell 20 from the positive mold 158. After this the clinician can prep and clean positive mold 158 removing all waste material and redressing positive mold 158 with an additional stockinet 116E (not shown).

Figure 9B:
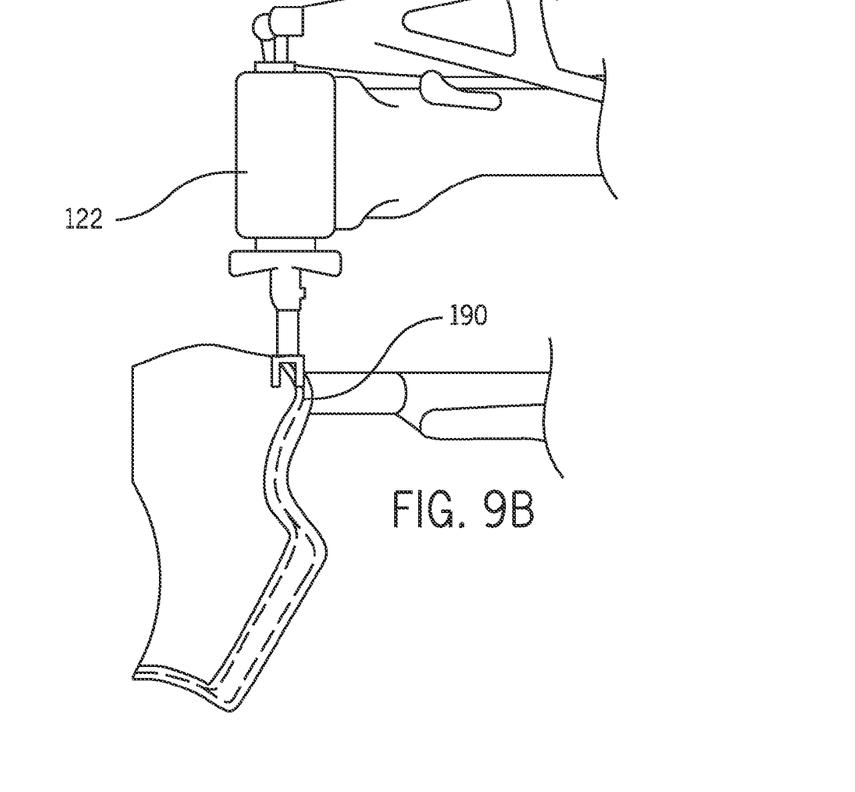
FIG. 9B shows a process step involved in producing an embodiment of the invention.

Turning to FIG. 9B, the clinician can sew along trim line 190 and along the laces stays to fully seal the plastic shell 160 into shell 20. At this point, the clinician can mark the desired eyelet 18 placement and using a rotary punch, make appropriate holes through both leather liner 182 and liner 184. Using an eyelet setter, the clinician can set eyelets 18 into place. After this, the clinician can place shell 20 back onto positive mold 158 with the toes facing toward the clinician and make marks across instep overlapping above and below the lace stays ⅛ of an inch. This indicates proper size and placement of tongue 14.

Following this, the clinician can remove shell 20 from positive mold 158 and cut lining leather 182 and leather 184 to a proper size and cement together them together. The clinician can hold to the tongue marks and then cut tongue 14 to an exact size and shape. After this, the clinician can sew the edges of tongue 14. The clinician can then cement and then sew tongue 14 into place in shell 20. Turning to FIG. 1, the clinician can finally lace up foot brace with appropriate length lace.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A foot brace configured to be worn beneath a patient's ankle providing therapeutic value to a patient, the foot brace comprising:
    a shell formed to a patient's foot and comprising a lateral counter extending downward from a midfoot region on the shell then upward toward a rearfoot portion of the shoe in a first section; a medial counter extending downward from a midfoot region on the shell then upward toward a rearfoot portion of the shoe, a second section; and an Achilles groove, extending downward from the first section and the second section; wherein the medial counter, the lateral counter and the Achilles groove are formed to place pressure on at least some portions of the patient's foot;

a lining mechanically coupled to the shell, a portion of the lining mechanically coupled to a midfoot instep closure which extends upward from the lateral counter, wherein the midfoot instep closure is configured to place pressure on a portion of the patient's foot;

a rearfoot extrinsic post mechanically coupled to the shell, wherein the rearfoot extrinsic post is configured to place pressure on a rear portion of the patient's foot.

2. The foot brace of claim 1, wherein the midfoot instep closure further comprises a tongue affixed to the lining, the midfoot instep closure further comprising a plurality of eyelets that can accommodate laces, which can be tightened or loosened to respectively increase or decrease pressure on the tongue, which can assist the shell and the rearfoot extrinsic post in providing therapeutic value to the patient.

3. The foot brace of claim 1, wherein a bottom of the shell is covered with a rearfoot liner and further covered with an interior lining to provide comfort for the patient; and a comfort material is placed on the medial and lateral sides of the shell for being proximate the patient provides further comfort for the patient.

4. A method of making a foot brace configured to be worn discretely beneath a patient's shoe while simulating therapeutic effects normally associated with over-the-ankle braces, the method comprising:

casting a negative model of a patient's foot;

filling the negative model with a casting material that hardens into a positive mold;

forming a shell upon the positive mold; wherein the shell further comprises: a lateral counter extending downward from a midfoot region on the shell then upward toward a rearfoot portion of the shoe in a first section; a medial counter extending downward from a midfoot region on the shell then upward toward a rearfoot portion of the shoe a second section; and an Achilles groove, extending downward from the first section and the second section; wherein the medial counter, the lateral counter and the Achilles groove are formed to place pressure on at least some portions of the patient's foot;

attaching a rearfoot extrinsic post to the shell;

covering an interior of the shell with an interior lining;

covering an exterior of the shell with a lining; and attaching a midfoot instep closure to the interior lining.

5. The method of claim 4, further comprising examining the patient's foot to identify landmarks, marking those landmarks on a stockinet; and transferring those landmarks onto the positive mold.

6. The method of claim 4, further comprising drawing negative pressure to cause the shell to conform to the exterior of the positive mold.

* * * * *